United States Patent
Fukushima et al.

(10) Patent No.: US 11,992,192 B2
(45) Date of Patent: May 28, 2024

(54) ENDOSCOPE APPARATUS

(71) Applicant: OLYMPUS CORPORATION, Tokyo (JP)

(72) Inventors: Ikutoshi Fukushima, Tokyo (JP); Junichi Nishimura, Tokyo (JP); Atsuyoshi Shimamoto, Tokyo (JP); Mitsuru Namiki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 529 days.

(21) Appl. No.: 17/154,083

(22) Filed: Jan. 21, 2021

(65) Prior Publication Data
US 2021/0161364 A1    Jun. 3, 2021

Related U.S. Application Data

(63) Continuation of application No. PCT/JP2018/027467, filed on Jul. 23, 2018.

(51) Int. Cl.
*A61B 1/00* (2006.01)
*A61B 1/04* (2006.01)
(Continued)

(52) U.S. Cl.
CPC .......... *A61B 1/042* (2013.01); *A61B 1/00009* (2013.01); *A61B 1/00013* (2013.01);
(Continued)

(58) Field of Classification Search
CPC ... A61B 1/042; A61B 1/00194; A61B 1/0655; A61B 1/00009; A61B 1/00013; A61B 1/00167; A61B 1/05; A61B 1/0661
(Continued)

(56) References Cited

U.S. PATENT DOCUMENTS 5,471,553 A * 11/1995 Teshima ................. B29C 48/34
385/115
8,083,726 B1 * 12/2011 Wang ................... A61L 27/3873
623/1.38
(Continued)

FOREIGN PATENT DOCUMENTS

EP       2322953 A1   5/2011
JP    2010-032425 A   2/2010
(Continued)

OTHER PUBLICATIONS

International Search Report dated Aug. 21, 2018 issued in PCT/JP2018/027467.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

An endoscope apparatus includes: a light source that radiates a pulsed light beam onto an imaging subject; an imaging optical system; an image transmission optical system that transmits the image of the imaging subject; an optical sensor that has a light receiving surface on which a plurality of pixels are arrayed and that detects a light level of the image; and one or more processors, wherein the optical sensor obtains light levels by detecting, in a time division manner, a reflected light beam of the pulsed light beam at each of the pixels, and wherein the processors are configured to: calculate an observation distance to the imaging subject from the imaging optical system on a basis of the light levels.

13 Claims, 14 Drawing Sheets

(51) Int. Cl.
  *A61B 1/05* (2006.01)
  *A61B 1/06* (2006.01)
(52) U.S. Cl.
  CPC ...... *A61B 1/00167* (2013.01); *A61B 1/00194* (2022.02); *A61B 1/05* (2013.01); *A61B 1/0655* (2022.02); *A61B 1/0661* (2013.01)
(58) Field of Classification Search
  USPC ........................................................ 600/160
  See application file for complete search history.

(56) References Cited

U.S. PATENT DOCUMENTS

| | | |
|---|---|---|
| 2011/0157354 A1 | 6/2011 | Kawahito |
| 2013/0162775 A1 | 6/2013 | Baumann et al. |
| 2015/0294463 A1 | 10/2015 | Takahashi |
| 2017/0105258 A1* | 4/2017 | Sakai .................. A61B 1/04 |
| 2018/0020960 A1* | 1/2018 | Sarussi .............. G01N 33/4925 |
| | | 600/310 |

FOREIGN PATENT DOCUMENTS

| | | |
|---|---|---|
| JP | 2010-169405 A | 8/2010 |
| JP | 2014-144034 A | 8/2014 |
| WO | WO 2016/181452 A1 | 11/2016 |

\* cited by examiner

ENDOSCOPE APPARATUS

CROSS-REFERENCE TO RELATED APPLICATIONS

This is a continuation of International Application PCT/JP2018/027467, with an international filing date of Jul. 23, 2018, which is hereby incorporated by reference herein in its entirety.

TECHNICAL FIELD

The present invention relates to an endoscope apparatus.

BACKGROUND ART

In the related art, there is a known endoscope apparatus having a function for measuring a distance to an imaging subject (for example, see Patent Literature 1). The endoscope apparatus of Patent Literature 1 includes a laser light source and a time-of-flight (ToF)-type distance measuring sensor. The ToF-type distance measuring sensor measures the distance on the basis of a time $\Delta t$ from when laser light starts to be shone to when reflected laser light is detected. In addition, with the endoscope apparatus of Patent Literature 1, laser light diffused by means of a lens is radiated onto an imaging-subject surface and, as a result of detecting reflected light beams coming from individual positions of the imaging-subject surface, distance information of the respective positions of the imaging-subject surface is acquired without scanning the laser light.

CITATION LIST

Patent Literature

{PTL 1} Japanese Unexamined Patent Application, Publication No. 2014-144034

SUMMARY OF INVENTION

One aspect of the present invention is directed to an endoscope apparatus including: a light source that radiates a pulsed light beam onto an imaging subject from a distal end of an insertion portion; an imaging optical system that is disposed at a distal-end portion of the insertion portion and that forms an image of the imaging subject by imaging a reflected light beam of the pulsed light beam coming from the imaging subject; an image transmission optical system that is disposed along a longitudinal direction inside the insertion portion and that transmits the image of the imaging subject to a proximal-end side of the insertion portion; an optical sensor that has a light receiving surface on which a plurality of pixels are arrayed and that detects, by means of each of the plurality of pixels, a light level of the image transmitted to the light receiving surface by the image transmission optical system; and one or more processors comprising hardware, wherein the optical sensor obtains a first light level and a second light level by detecting, in a time division manner, the reflected light beam at each of the pixels, the first light level being a light level of the reflected light beam accumulated during a first period, the second light level being a light level of the reflected light beam accumulated during a second period, and wherein the one or more processors are configured to: calculate a distance from the first light level and the second light level, which are detected by the optical sensor at each of the pixels, and calculate an observation distance to each of the positions of the imaging subject from the imaging optical system by subtracting a correction value from the calculated distance, the correction value being set on a basis of the depth to which the pulsed light beam is transmitted into the imaging subject.

Another aspect of the present invention is directed to an endoscope apparatus including: a radiating portion that radiates a pulsed light beam onto an imaging subject from a distal end of an insertion portion; an imaging optical system that is disposed at a distal-end portion of the insertion portion and that forms an image of the imaging subject by imaging a reflected light beam of the pulsed light beam coming from the imaging subject; an image transmission optical system that is disposed along a longitudinal direction inside the insertion portion and that transmits the image of the imaging subject to a proximal-end side of the insertion portion; an optical sensor that has a light receiving surface on which a plurality of pixels are arrayed and that detects, by means of each of the plurality of pixels, a light level of the image transmitted to the light receiving surface by the image transmission optical system; and one or more processors comprising hardware, wherein the radiating portion comprises: a light source that is disposed on the proximal-end side of the insertion portion and that emits the pulsed light beam, a first optical fiber that is disposed along the longitudinal direction inside the insertion portion and that guides the pulsed light beam to the distal end of the insertion portion, a half mirror that is provided at the distal-end portion of the insertion portion and that generates a reference light beam by reflecting a portion of the pulsed light beam, and a second optical fiber that guides the reference light beam to the optical sensor from the first optical fiber, wherein the optical sensor obtains a first light level and a second light level by detecting, in a time division manner, the reflected light beam at each of the pixels, the first light level being a light level of the reflected light beam accumulated during a first period, the second light level being a light level of the reflected light beam accumulated during a second period, and wherein the one or more processors are configured to calculate an observation distance to each of the positions of the imaging subject from the imaging optical system on a basis of the first light level and the second light level, which are detected by the optical sensor at each of the pixels.

DESCRIPTION OF EMBODIMENTS

First Embodiment

An endoscope apparatus according to a first embodiment of the present invention will be described with reference to the drawings.

Figure 1:
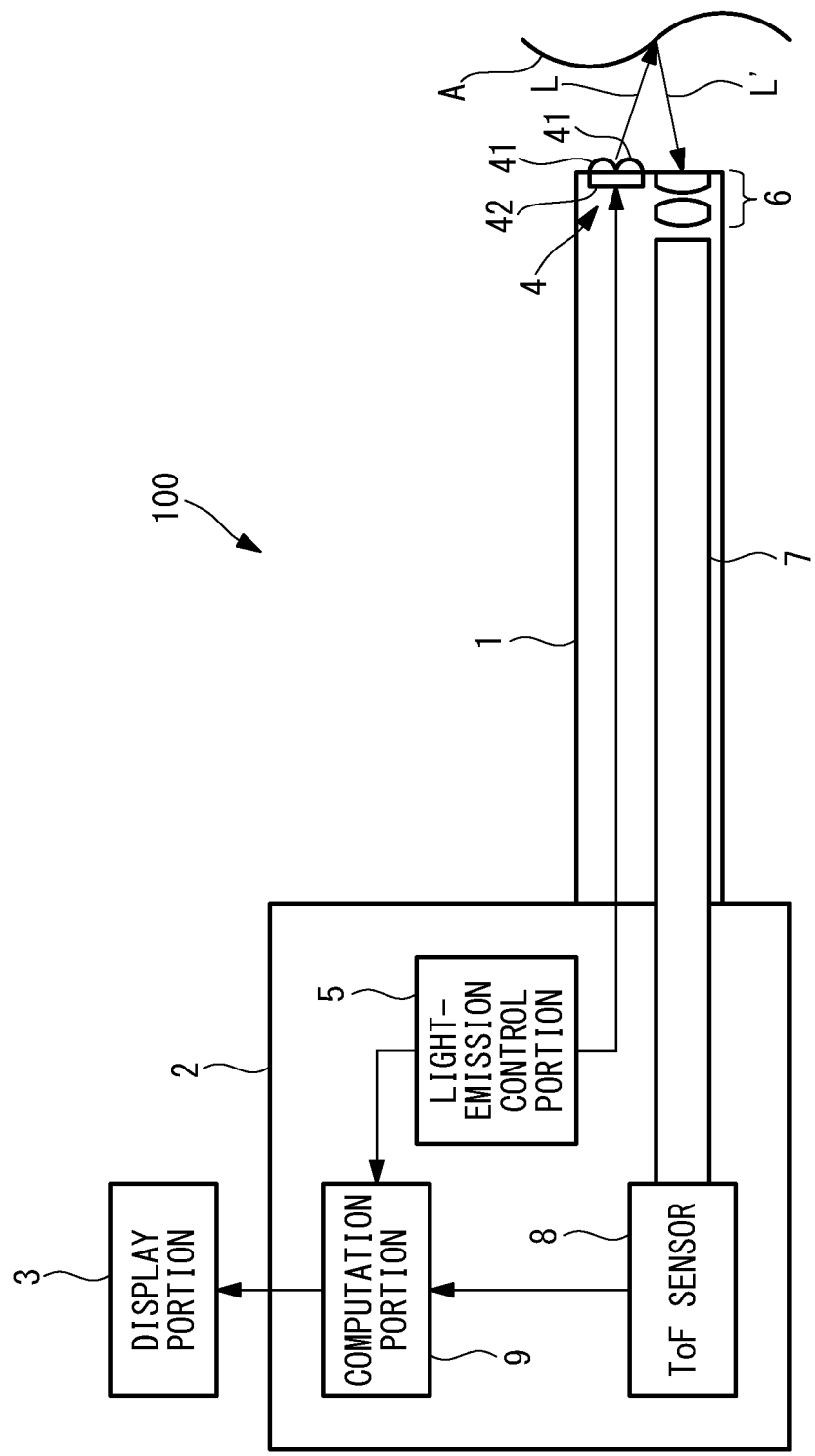
FIG. 1 is an overall configuration diagram of an endoscope apparatus according to a first embodiment of the present invention.

As shown in FIG. 1, an endoscope apparatus 100 according to this embodiment includes: an elongated insertion portion 1 that is inserted into an observation target having an imaging subject A; a main body portion 2 that is connected to a proximal end of the insertion portion 1; and a display portion 3 that is connected to the main body portion 2. In addition, the endoscope apparatus 100 includes: a radiating portion 4; a light-emission control portion 5; an imaging optical system 6; an image transmission portion 7; an optical sensor 8; and a computation portion 9. The radiating portion 4, the imaging optical system 6, and the image transmission portion 7 are disposed inside the insertion portion 1. The light-emission control portion 5, the optical sensor 8, and the computation portion 9 are disposed inside the main body portion 2.

The radiating portion 4 includes a small light source 41 such as an LED and a control circuit 42 that is integrally provided with the light source 41 and that controls the light source 41. The light source 41 is disposed at a distal end of the insertion portion 1. There may be just one light source 41, or more than one. The control circuit 42 is connected to the light-emission control portion 5 and causes the light source 41 to generate pulsed light beams L in response to control signals coming from the light-emission control portion 5. The pulsed light beams L generated by the light source 41 are radiated onto the imaging subject A facing the distal end of the insertion portion 1. The pulsed light beams L are divergent light beams and are radiated in a two-dimensional region on the surface of the imaging subject A.

The light-emission control portion 5 generates the control signals for controlling pulse widths ΔW, the light levels, and so forth of the pulsed light beams L and transmits the control signals to the control circuit 42. The light-emission control portion 5 causes the light source 41 to generate the pulsed light beams L in a constant time cycle by transmitting the control signals to the control circuit 42 in the constant time cycle.

The imaging optical system 6 includes a single lens or a plurality of lenses and is provided in a distal-end portion of the insertion portion 1. The imaging optical system 6 has a viewing field that includes a measurement region of the imaging subject A onto which the pulsed light beams L are radiated. The imaging optical system 6 receives reflected light beams L' of the pulsed light beams L coming from the imaging subject A, causes the reflected light beams L' to form an image, and forms an image of the imaging subject A. The reflected light beams L' are light beams of a pulsed form having time widths corresponding to the pulse widths ΔW. In endoscopy, there are cases in which the imaging subject A is observed in a state in which a distal end of the insertion portion 1 is in contact with the imaging subject A or a state in which the distal end of the insertion portion 1 is in the close proximity to the imaging subject A. The imaging optical system 6 is capable of observing both a near point image and a far point image and has an observation distance of, for example, 0 to 100 mm.

The image transmission portion 7 is an optical system that transmits optical images and is, for example, an optical-fiber bundle or a relay optical system. The image transmission portion 7 is disposed inside the insertion portion 1 over substantially the entire length of the insertion portion 1 and optically connects the imaging optical system 6 and the optical sensor 8 in the main body portion 2. The image transmission portion 7 transmits the image of the imaging subject A formed by the imaging optical system 6 to a light receiving surface of the optical sensor 8 and re-images an image on the light receiving surface. The image of the imaging subject A is formed on the light receiving surface of the ToF sensor 8 over a period corresponding to the pulse width of a pulsed light beam L. The image transmission portion 7 preferably has an optical-path length that is equal to or greater than the maximum observation distance of the imaging optical system 6. For example, the length of each of the insertion portion 1 and the image transmission portion 7 is 2 m.

Figure 2:
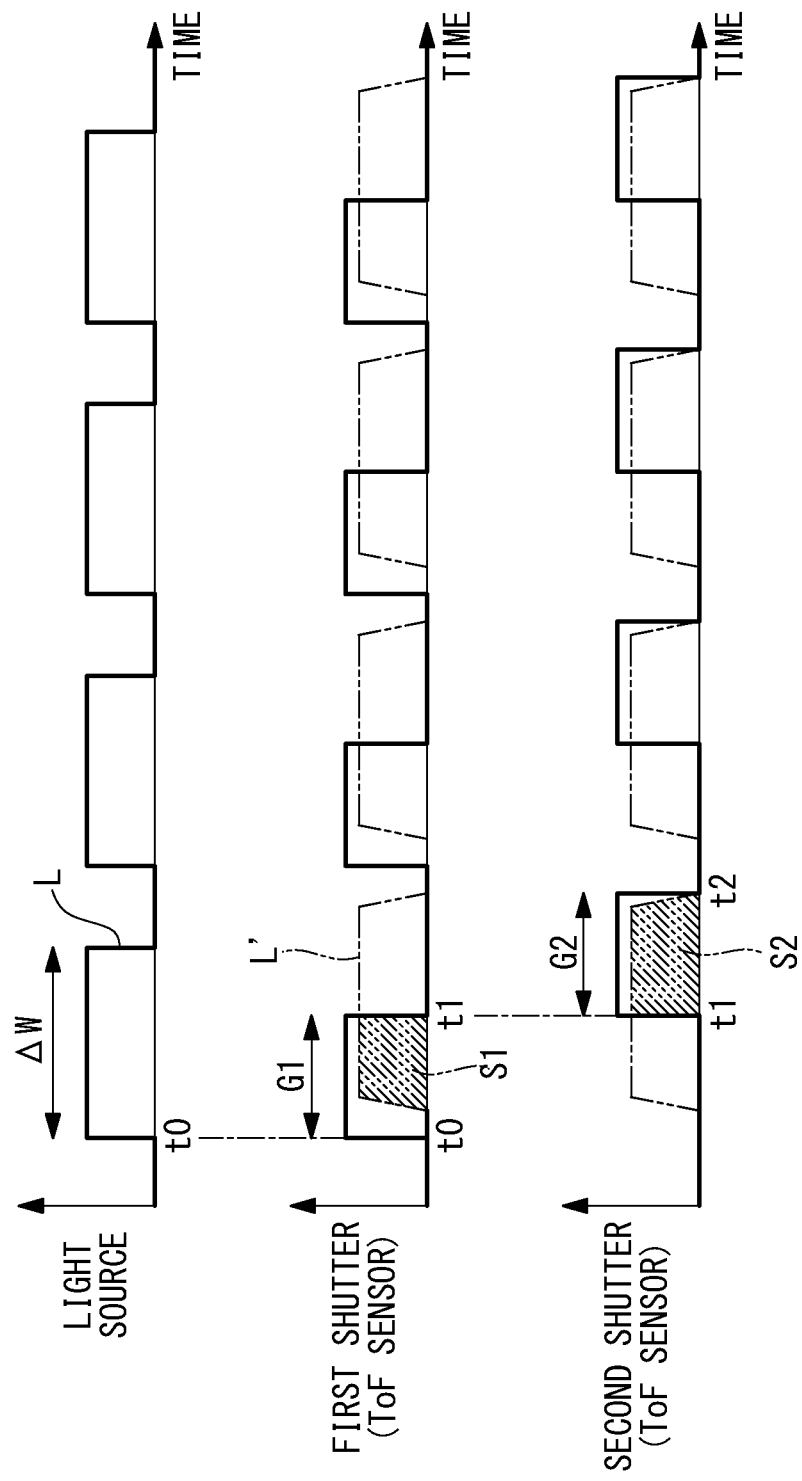
FIG. 2 is a timing chart showing the operation of a light source and a ToF sensor of the endoscope apparatus in FIG. 1.

The optical sensor 8 is a two-dimensional indirect ToF (Time of Flight) sensor having a two-dimensional array of a plurality of pixels. The two-dimensional array is provided in the light receiving surface. FIG. 2 shows the operation of the respective pixels of the ToF sensor 8. The reflected light beams L' reach the ToF sensor 8 with the same time cycle as the time cycle of the pulsed light beams L. The ToF sensor 8 detects the light levels of the image of the imaging subject A on the light receiving surface by means of the respective pixels of the two-dimensional array in synchronization with the cycle with which the pulsed light beams L are emitted from the radiating portion 4.

The respective pixels detect the light level of one reflected light beam L' during one detection period. The length of one detection period is set, on the basis of the pulse width ΔW, to be a length that includes the entirety of one reflected light beam L'. In addition, one detection period is divided into two equal periods (a first gate G1 and a second gate G2). The first gate G1 and the second gate G2 respectively correspond to the first period and the second period of the present invention. As a result of detecting the light level of the one reflected light beam L' in the first gate G1 and the second gate G2 in a time division manner, the respective pixels obtain an accumulated light level S1 of the reflected light beam L' in the first gate G1 and an accumulated light level S2 of the reflected light beam L' in the second gate G2.

The first gate G1 is a period from a time t0 to a time t1, and the second gate G2 is a period from the time t1 to a time t2. The time t0 is the time at which the light source 41 generates a pulsed light beam L. The time t2 is the time between the terminal end of a reflected light beam L' and an initial end of the next reflected light beam L'. Each of the pixels accumulates the light levels of the reflected light beams L' from the time t0 to the time t1 in accordance with control by a first shutter and obtains an accumulated light level of the reflected light beams L' so as to serve as a first light level S1. Next, each of the pixels accumulates the light levels of the reflected light beams L' from the time t1 to the time t2 in accordance with control by a second shutter and obtains an accumulated light level of the reflected light beams L' so as to serve as a second light level S2.

Here, a delay time $\Delta t$ occurs between when the light source 41 generates the pulsed light beam L at the time t0 and when the initial end of the reflected light beam L' reaches the ToF sensor 8. The delay time $\Delta t$ depends on an observation distance D to each of the positions of the imaging subject A from the distal end of the imaging optical system 6. Therefore, the first light level S1 and the second light level S2 change in accordance with the observation distance D. In other words, the delay time $\Delta t$ increases with an increase in the observation distance D, and, as a result, the first light level S1 decreases and the second light level S2 increases. In contrast, the delay time $\Delta t$ decreases with a decrease in the observation distance D, and, as a result, the first light level S1 increases and the second light level S2 decreases.

The computation portion 9 calculates a ratio S1/S2 of the first light level to the second light level S2 from the first light level S1 and the second light level S2 detected at each of the pixels. Next, the computation portion 9 calculates the delay times $\Delta t$ from the ratio S1/S2 and calculates the observation distance D from the delay times $\Delta t$.

The computation portion 9 calculates the observation distances D from the light levels S1 and S2 detected by all of the pixels. The computation portion 9 creates a two-dimensional distance map in which the respective pixels have values corresponding to the observation distances D, and causes the display portion 3 to display the distance map. For example, the respective pixels of the distance map have colors in accordance with the observation distances D.

The display portion 3 is a display device of an arbitrary type and is, for example, a liquid crystal display.

The light-emission control portion 5 and the computation portion 9 are realized by means of a processor and a storage device provided inside the main body portion 2. In other words, the storage device stores a control program and a calculation program. The processor executes the above-described control processing performed by the light-emission control portion 5 in accordance with the control program and executes the above-described calculation processing performed by the computation portion 9 in accordance with the calculation program.

Next, the operation of the thus-configured endoscope apparatus 100 will be described.

With the endoscope apparatus 100 according to this embodiment, the pulsed light beams L generated by the radiating portion 4 are radiated to the imaging subject A from the distal end of the insertion portion 1 and an image of the imaging subject A based on the reflected light beams L' is formed by the imaging optical system 6. The image is transmitted to the ToF sensor 8 in the main body portion 2 from the imaging optical system 6 at the distal end of the insertion portion 1 by means of the image transmission portion 7 and the image of the imaging subject A is re-imaged on the light receiving surface of the ToF sensor 8.

The ToF sensor 8 and the computation portion 9 measure, by means of the indirect ToF system, the observation distances D between the imaging optical system 6 and the respective positions of the imaging subject A.

Specifically, each of the pixels of the ToF sensor 8 detects the light levels of the image of the imaging subject A in a time division manner in the time gates G1 and G2. In other words, each of the pixels detects the first light level S1 by accumulating the light levels of the reflected light beams L' in the first gate G1 and subsequently detects the second light level S2 by accumulating the light levels of the reflected light beams L' in the second gate G2.

Next, in the computation portion 9, the observation distance D to each of the positions on the surface of the imaging subject A corresponding to each of the pixels is calculated from the ratio S1/S2 detected by each of the pixels. Next, in the computation portion 9, the two-dimensional distance map is created from the observation distances D of all of the pixels, and the distance map is displayed on the display portion 3.

Here, the measurement precision of the observation distance D will be described.

In the case in which the imaging subject A has unevenness, the observation distances D become variable. In order to accurately measure the observation distances D in the entire measurement region of the imaging subject A regardless of the magnitudes of the observation distances D, it is important that the light levels S1 and S2 do not change greatly regardless of changes in the observation distances D. The light levels S1 and S2 are proportional to the gate widths $\Delta G1$ and $\Delta G2$. The gate width $\Delta G1$ is the time width $(=t1-t2)$ of the first gate G1, and the gate width $\Delta G2$ is the time width $(=t2-t1=\Delta G1)$ of the second gate G2.

An optimal gate width $\Delta G1$, $\Delta G2$ for serving as a near point is $\Delta W/2+\Delta t\min$ and an optimal gate width $\Delta G1$, $\Delta G2$ for serving as a far point is $\Delta W/2+\Delta t\max$. Here $\Delta t\min$ is the delay time at the nearest point and $\Delta t\max$ is the delay time at the farthest point. In order to suppress changes in the light level S1, S2, it is necessary to decrease an appropriate gate width ratio $(\Delta W/2+\Delta t\min)/(\Delta W/2+\Delta t\max)$ of the near point to the far point. In the distance measurement by the endoscope apparatus 100, the observation distances D are approximately 0-300 mm, and the $\Delta t\min$ approaches zero at the near point. Therefore, it is difficult to decrease the above-described ratio in principle.

With this embodiment, the ToF sensor 8 is disposed at a position away from the imaging optical system 6 at the distal end of the insertion portion 1 in the longitudinal direction of the insertion portion 1. In addition, the reflected light beam L' is guided by the long image transmission portion 7 to the ToF sensor 8 on the proximal-end side of the insertion portion 1 from the imaging optical system 6 at the distal end of the insertion portion 1. Accordingly, the optical-path length of the reflected light beam L' is ensured to have a length corresponding to the length of the insertion portion 1, and the delay time $\Delta t$ is ensured to have a constant magnitude even if the observation distance D is zero or substantially zero. Furthermore, the indirect ToF system that calculates the delay time $\Delta t$ from the ratio S1/S2 is capable of measuring a low delay time $\Delta t$ at a high precision as compared with a direct ToF system that directly measures the delay time $\Delta t$. As described above, as a result of ensuring the optical-path length of the reflected light beam L' in the insertion portion 1 and of employing an indirect ToF system, there is an advantage in that it is possible to measure, at a high precision, an observation distance D that is zero or close to zero.

In addition, the two-dimensional image of the imaging subject A is formed on the light receiving surface of the ToF sensor 8, and the observation distance D to each of the positions on the surface of the imaging subject A is measured by each of the pixels. As described above, there is an advantage in that it is possible to obtain the two-dimensional distance information of the imaging subject A without two-dimensionally scanning the laser light. In addition, on the basis of the distance map, for example, it is possible to obtain tumor shape information in the medical field and it is possible to obtain shape and depth information of a crack in a structure in the industrial field.

It is preferable that a length P0 of the image transmission portion 7 through which the pulsed light beam L and the reflected light beam L' travel in the insertion portion 1 and the main body portion 2 be greater than a maximum observation distance D (P0>D). For example, in the case in which observation distances D of 0-300 mm are measurement targets, it is preferable to satisfy P0>300 mm. As a result of satisfying this condition, the ratio of Δtmin to the Δtmax decreases even in the state in which the observation distances D are zero or close to zero. Accordingly, it is possible to obtain the ratios S1/S2 in an appropriate range in the entire measurement region of the imaging subject A, and it is possible to stabilize the measurement precision of the observation distances D.

It is preferable that the pulse width ΔW of the pulsed light beam L satisfy the expression below:

$$\Delta W[s] > n \times P0[m]/c[m/s],$$

where n is the refractive index of the optical path through which the pulsed light beam L and the reflected light beam L' travel in the insertion portion 1 and the main body portion 2, and is, for example, the refractive index of the image transmission portion 7; and c is the light speed of the pulsed light beam L.

Figure 3:
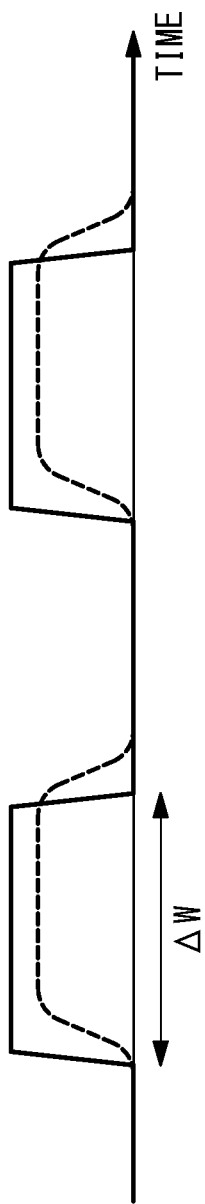
FIG. 3 is a diagram showing the influences of the mode dispersion and the light-level attenuation on reflected light beams L' in the case in which an optical-fiber bundle is employed in an image transmission portion of the endoscope apparatus in FIG. 1.

In the case in which an optical-fiber bundle is employed as the image transmission portion 7, a delay occurs in a reflected light beam L' to be detected and the light level thereof decreases due to mode dispersion and light-level attenuation that the optical-fiber bundle possesses, as shown in FIG. 3. In FIG. 3, the solid line indicates the reflected light beams L' in the case in which there is no influence of mode dispersion and light-level attenuation due to the optical-fiber bundle, and the broken line indicates the reflected light beams L' in the case in which there are influences of mode dispersion and light-level attenuation due to the optical-fiber bundle. In order to decrease the influences of mode dispersion and light-level attenuation and to measure the first light levels S1 and the second light levels S2 of the reflected light beams L' at a high precision, it is necessary to also increase the pulse width ΔW in correspondence with the optical-path length of the image transmission portion 7, and it is particularly preferable that the pulse width ΔW satisfy the above-described condition. As a result of satisfying the above-described conditional expression, the ratios S1/S2 take appropriate values regardless of the magnitude of the observation distances D without deteriorating the detection precision, and it is possible to measure the observation distances D in the entire measurement region of the imaging subject A at a high precision.

The computation portion 9 may calculate the sum of the light levels S1 and S2 in addition to calculating the observation distances D. The sum S1+S2 is a signal value of the image of the imaging subject A based on the intensity of the reflected light beam L'. The computation portion 9 may create a two-dimensional image of the imaging subject A on the basis of the signal value and may cause the display portion 3 to display the image simultaneously with the distance map. The distance map and the image may be saved in the storage device in the main body portion 2.

In the case of an imaging subject A possessing light transmitting properties, such as biological tissue, the pulsed light beam L penetrates into the interior of the imaging subject A from a surface thereof, is reflected in the interior of the imaging subject A, and is emitted from the surface of the imaging subject A. In such a case, a delay corresponding to the transmission depth in the imaging subject A occurs in the reflected light beam L', and a distance calculated from the ratio S1/S2 includes the transmission depth. The transmission depth of the pulsed light beam L in the imaging subject A depends on the wavelength of the pulsed light beam L and is, for example, approximately several millimeters.

The computation portion 9 may calculate the observation distance D in which the delay time based on penetration of the pulsed light beam L into the imaging subject A is taken into consideration. Specifically, the computation portion 9 stores a correction value. The correction value is a transmission depth (for example, 2 mm) of the pulsed light beam L that is experimentally or theoretically calculated and is set, for example, in the main body portion 2 by a user. The computation portion 9 calculates, as the observation distance D, values obtained by subtracting the correction value from the distance calculated from the ratio S1/S2. Accordingly, it is possible to more accurately calculate the observation distance D.

Figure 4:
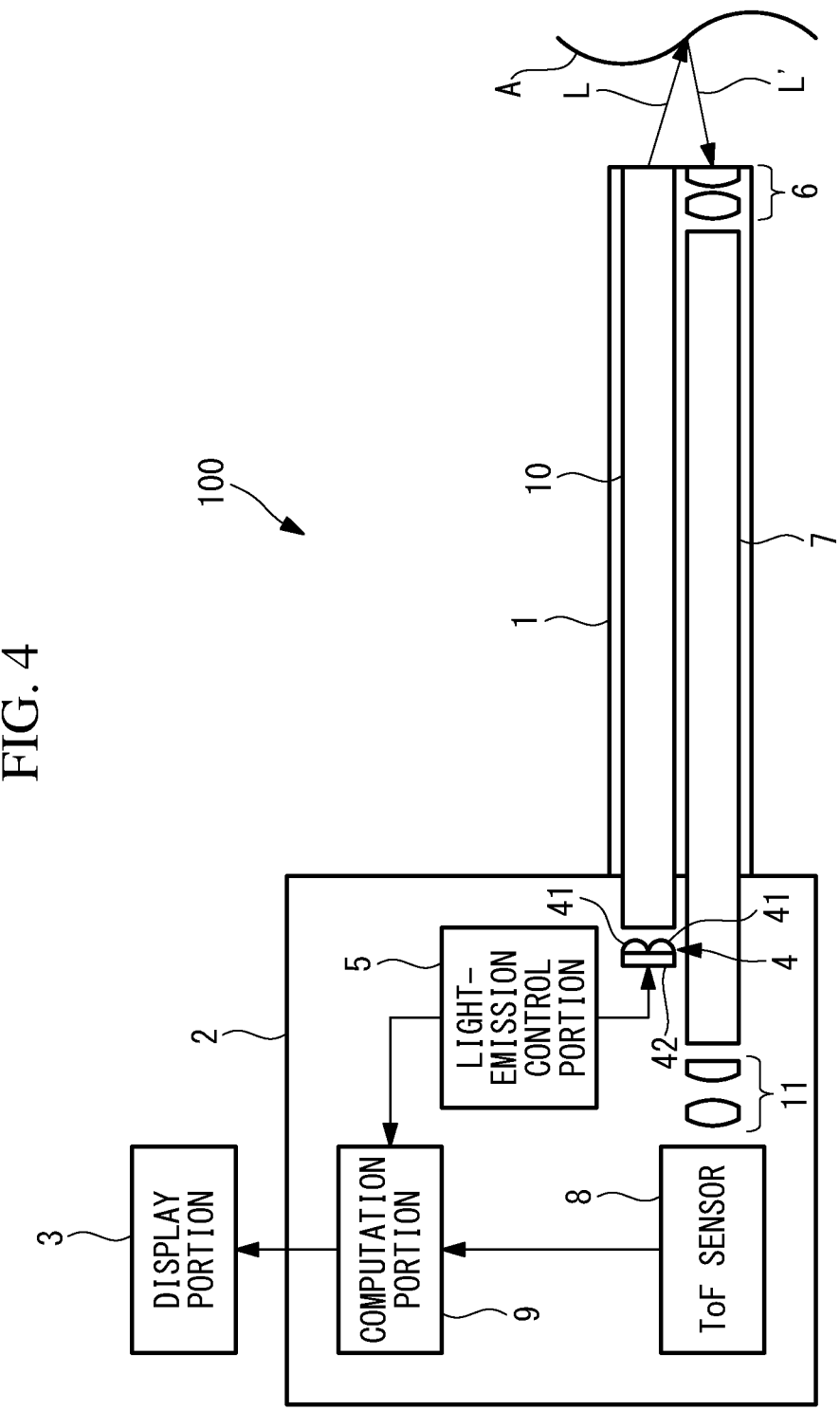
FIG. 4 is an overall configuration diagram of a modification of the endoscope apparatus in FIG. 1.

In this embodiment, the light source 41 is disposed in the distal-end portion of the insertion portion 1; however, alternatively, the light source 41 may be disposed inside the main body portion 2 and the radiating portion 4 may additionally include a light guide portion 10, as shown in FIG. 4.

The light guide portion 10 is an optical member that guides the pulsed light beam L and is, for example, an optical fiber or an optical-fiber bundle. The light guide portion 10 is disposed along the longitudinal direction of the insertion portion 1 and guides the pulsed light beam L to the distal end of the insertion portion 1 from the light source 41. As a result of eliminating the light source 41 and the control circuit 42 from the distal-end portion of the insertion portion 1, it is possible to make the distal-end portion of the insertion portion 1 thinner.

In the case in which the light guide portion 10 is provided, it is possible to increase the delay time Δt in correspondence to the optical-path length of the light guide portion 10.

In this embodiment, a re-imaging optical system 11 may be provided between the image transmission portion 7 and the ToF sensor 8, as shown in FIG. 4.

The re-imaging optical system 11 re-images the image transmitted by the image transmission portion 7 on the light receiving surface of the ToF sensor 8. As a result of employing the re-imaging optical system 11, the need to directly connect the proximal end of the image transmission portion 7 and the ToF sensor 8 is eliminated. Therefore, it is possible to enhance the degree of freedom in designing the ToF sensor 8 in terms of arrangement, type selection, and so forth. In addition, a sufficient optical-path length is ensured between the image transmission portion 7 and the ToF sensor 8, and the delay time Δt is further increased.

Second Embodiment

Next, an endoscope apparatus according to a second embodiment of the present invention will be described with reference to the drawings.

In this embodiment, configurations that are different from those of the first embodiment will be described, and configurations that are the same as those of the first embodiment will be given the same reference signs and descriptions thereof will be omitted.

Figure 5:
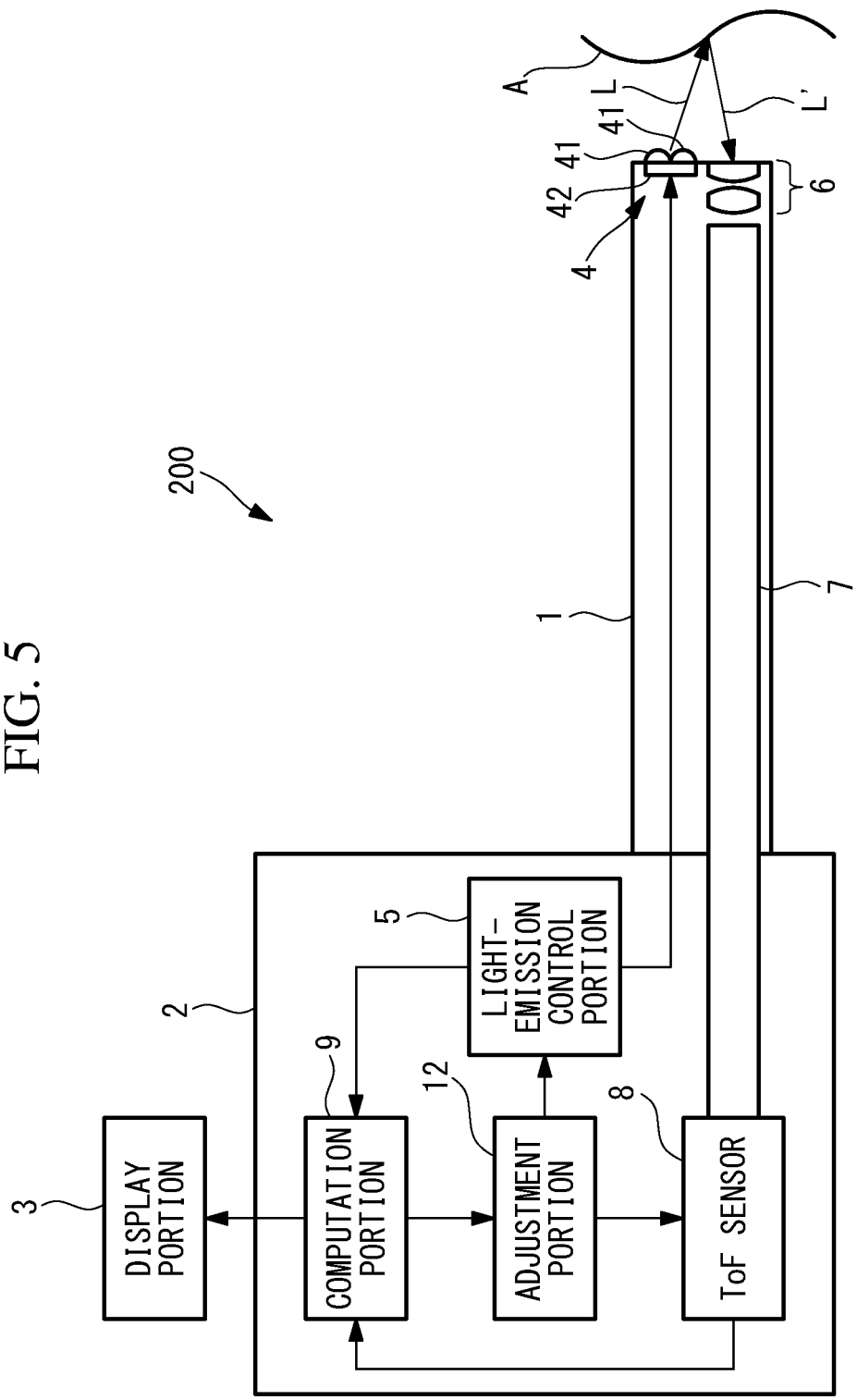
FIG. 5 is an overall configuration diagram of an endoscope apparatus according to a second embodiment of the present invention.

As shown in FIG. 5, an endoscope apparatus 200 according to this embodiment includes: the insertion portion 1; the main body portion 2; and the display portion 3. In addition, the endoscope apparatus 200 includes: the radiating portion 4; the light-emission control portion 5; the imaging optical system 6; the image transmission portion 7; the optical sensor 8; the computation portion 9; and an adjustment portion 12.

The adjustment portion 12 receives the ratio S1/S2 from the computation portion 9 and causes the light-emission control portion 5 and the ToF sensor 8 to execute adjustments of pulse width ΔW and gate widths ΔG1 and ΔG2 on the basis of the ratio S1/S2.

Figure 6:
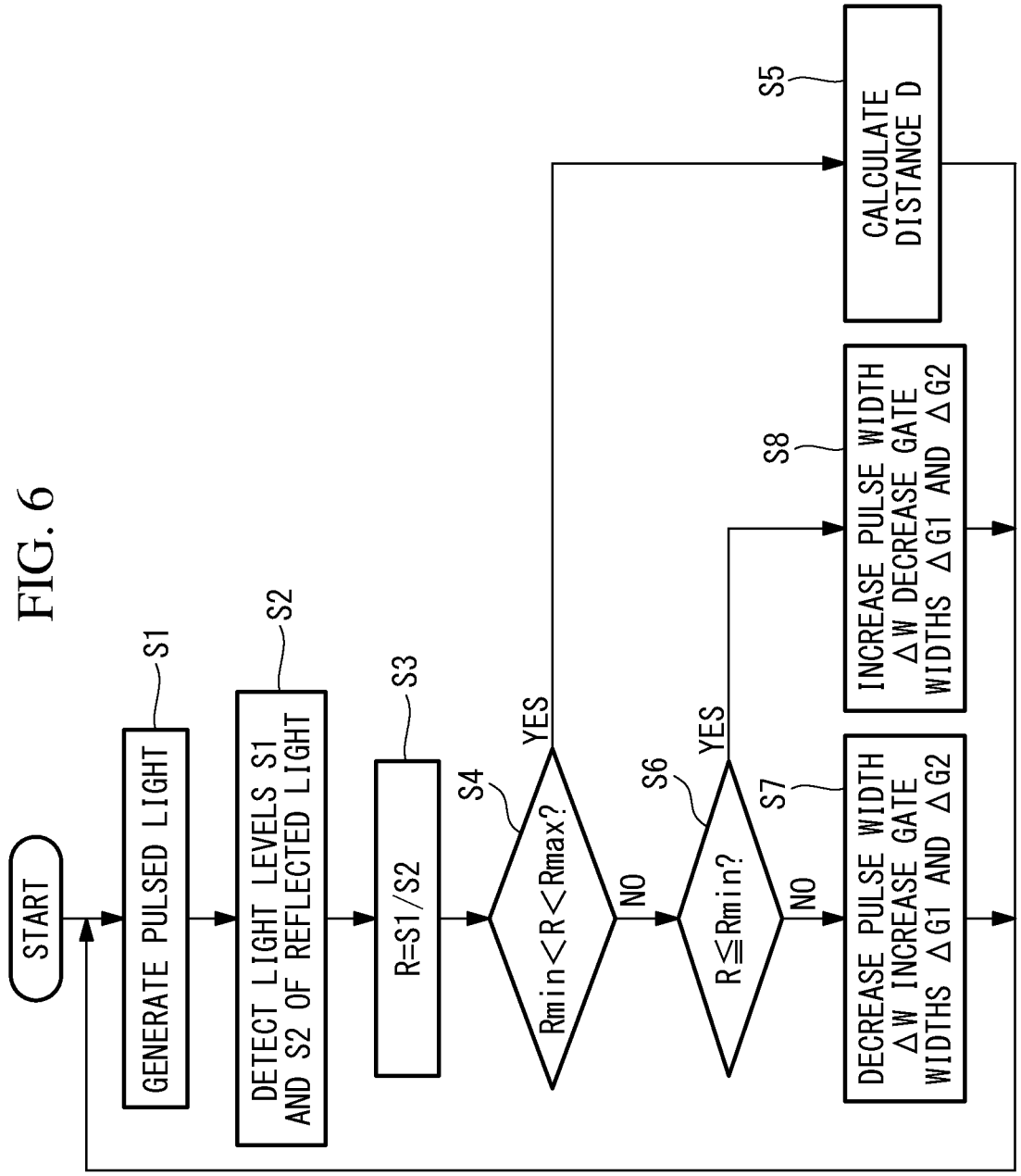
FIG. 6 is a flowchart showing the operation of the endoscope apparatus in FIG. 5.

FIG. 6 shows the operation of the endoscope apparatus 200 related to the adjustments of the pulse width ΔW and the gate widths ΔG1 and ΔG2.

As shown in FIG. 6, the pulsed light beam L is emitted from the light source 41 (step S1), the first light level S1 and the second light level S2 are detected by the ToF sensor 8 (step S2), and the ratio R=S1/S2 is calculated by the computation portion 9 (step S3). The adjustment portion 12 compares the ratio S1/S2 with a prescribed lower limit value Rmin and a prescribed upper limit value Rmax (Rmax>Rmin) (step S4).

In the case in which the ratio S1/S2 is greater than the lower limit value Rmin and less than the upper limit value Rmax ("YES" in step S4), the adjustments of the pulse width ΔW and the gate widths ΔG1 and ΔG2 by the adjustment portion 12 are not executed, and the observation distance D is calculated from the ratio S1/S2 by the computation portion 9 (step S5).

On the other hand, in the case in which the ratio S1/S2 is equal to or less than the lower limit value Rmin or equal to or greater than the upper limit value Rmax ("NO" in step S4), and the adjustments of the pulse width ΔW and the gate widths ΔG1 and ΔG2 by the adjustment portion 12 are executed (steps S6 to S8). Specifically, in the case in which the ratio S1/S2 is equal to or greater than the upper limit value Rmax ("NO" in step S6), the adjustment portion 12 decreases the pulse width ΔW and increases the gate widths ΔG1 and ΔG2 (step S7). In the case in which the ratio S1/S2 is equal to or less than the lower limit value Rmin ("YES" in step S6), the adjustment portion 12 increases the pulse width ΔW and decreases the gate widths ΔG1 and ΔG2 (step S8). The adjustments of the pulse width ΔW and the gate widths ΔG1 and ΔG2 are executed in accordance with adjustment signals that are respectively transmitted to the light-emission control portion 5 and the ToF sensor 8 from the adjustment portion 12.

After adjusting the pulse width ΔW and the gate widths ΔG1 and ΔG2, steps S1 to S4 are re-executed and the adjustments of the pulse width ΔW and the gate widths ΔG1 and ΔG2 are repeated until the ratio S1/S2 becomes greater than the lower limit value Rmin and less than the upper limit value Rmax. In steps S7 and S8, only one of the pulse width ΔW and gate widths ΔG1 and ΔG2 may be adjusted.

The adjustment portion 12 is realized by means of the processor and the storage device provided in the main body portion 2, as with the light-emission control portion 5 and the computation portion 9. The processor executes the above-described adjustment processing of the adjustment portion 12 in accordance with an adjustment program stored in the storage device.

In the case in which the ratios S1/S2 are excessively high or excessively low, the calculation precision of the observation distances D deteriorates. With this embodiment, in the case in which the ratios S1/S2 are equal to or greater than the upper limit value Rmax or equal to or less than the lower limit value Rmin, at least one of the pulse width ΔW and the gate widths ΔG1 and ΔG2 is adjusted so that the ratios S1/S2 falls within an appropriate range in which the ratios S1/S2 are greater than the lower limit value Rmin and less than the upper limit value Rmax, and the observation distances D are calculated from the adjusted ratios S1/S2. Accordingly, it is possible to measure the observation distances D at a higher precision in the entire measurement region of the imaging subject A.

Figure 7:
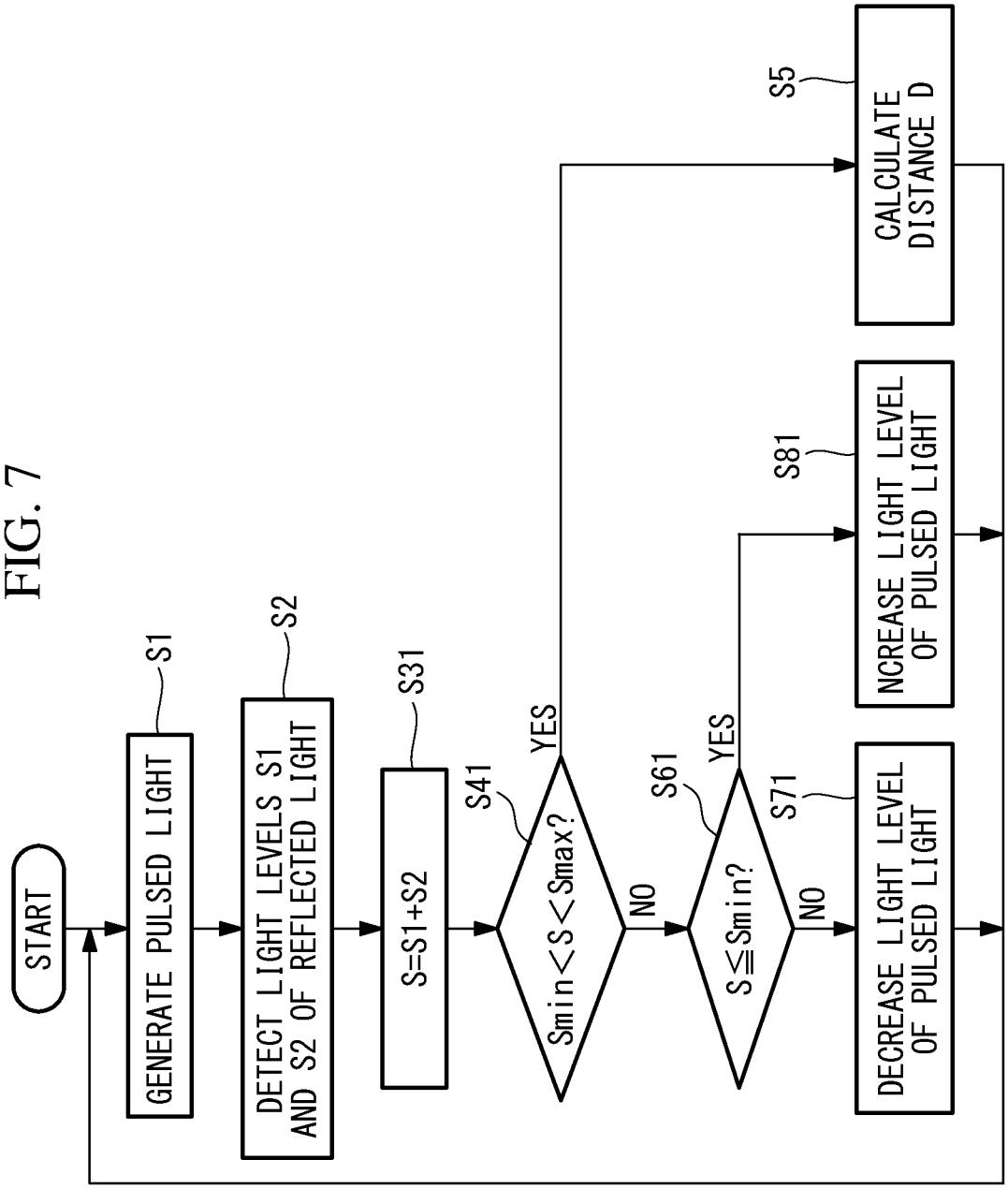
FIG. 7 is a flowchart showing a modification of the operation of the endoscope apparatus in FIG. 5.

In this embodiment, the adjustment portion 12 adjusts the pulse width ΔW and the gate widths ΔG1 and ΔG2 on the basis of the ratio S1/S2; however, alternatively, the light level of the pulsed light beam L may be adjusted on the basis of the sum S=S1+S2, as shown in FIG. 7.

The computation portion 9 calculates the sum S1+S2 (step S31). The adjustment portion 12 compares the sum S1+S2 with the prescribed lower limit value Smin and the prescribed upper limit value Smax (Smax>Smin) (step S41). In the case in which the sum S1+S2 is equal to or greater than the upper limit value Smax ("NO" in step S61), the adjustment portion 12 decreases the light level of the pulsed light beam L (step S71). On the other hand, in the case in which the sum S1+S2 is equal to or less than the lower limit value Smin ("YES" in step S61), the adjustment portion 12 increases the light level of the pulsed light beam L (step S81). The adjustment of the light level of the pulsed light beam L is executed in accordance with the adjustment signals transmitted to the light-emission control portion 5 from the adjustment portion 12.

In the case in which the sums S1+S2 are excessively high or excessively low, the calculation precision of the observation distances D deteriorates. With this modification, in the case in which the sums S1+S2 are equal to or greater than the upper limit value Smax or equal to or less than the lower limit value Smin, as a result of the light levels of the pulsed light beams L being adjusted by the adjustment portion 12, the sums S1+S2 are adjusted within an appropriate range in which the sums S1+S2 are greater than the lower limit value Smin and less than the upper limit value Smax. By adjusting the light levels of the pulsed light beams L on the basis of the sums S1+S2 in this way also, it is possible to measure the observation distances D at a higher precision in the entire measurement region of the imaging subject A.

The light levels S1 and S2 depend on the gate widths ΔG1 and ΔG2. Therefore, the adjustment portion 12 may adjust the gate widths ΔG1 and ΔG2 in steps S71 and S81 instead of the light level of the pulsed light beam L.

Third Embodiment

Next, an endoscope apparatus according to a third embodiment of the present invention will be described with reference to the drawings.

In this embodiment, configurations that are different from those of the first and second embodiments will be described, and configurations that are the same as those of the first and second embodiments will be given the same reference signs and descriptions thereof will be omitted.

Figure 8:
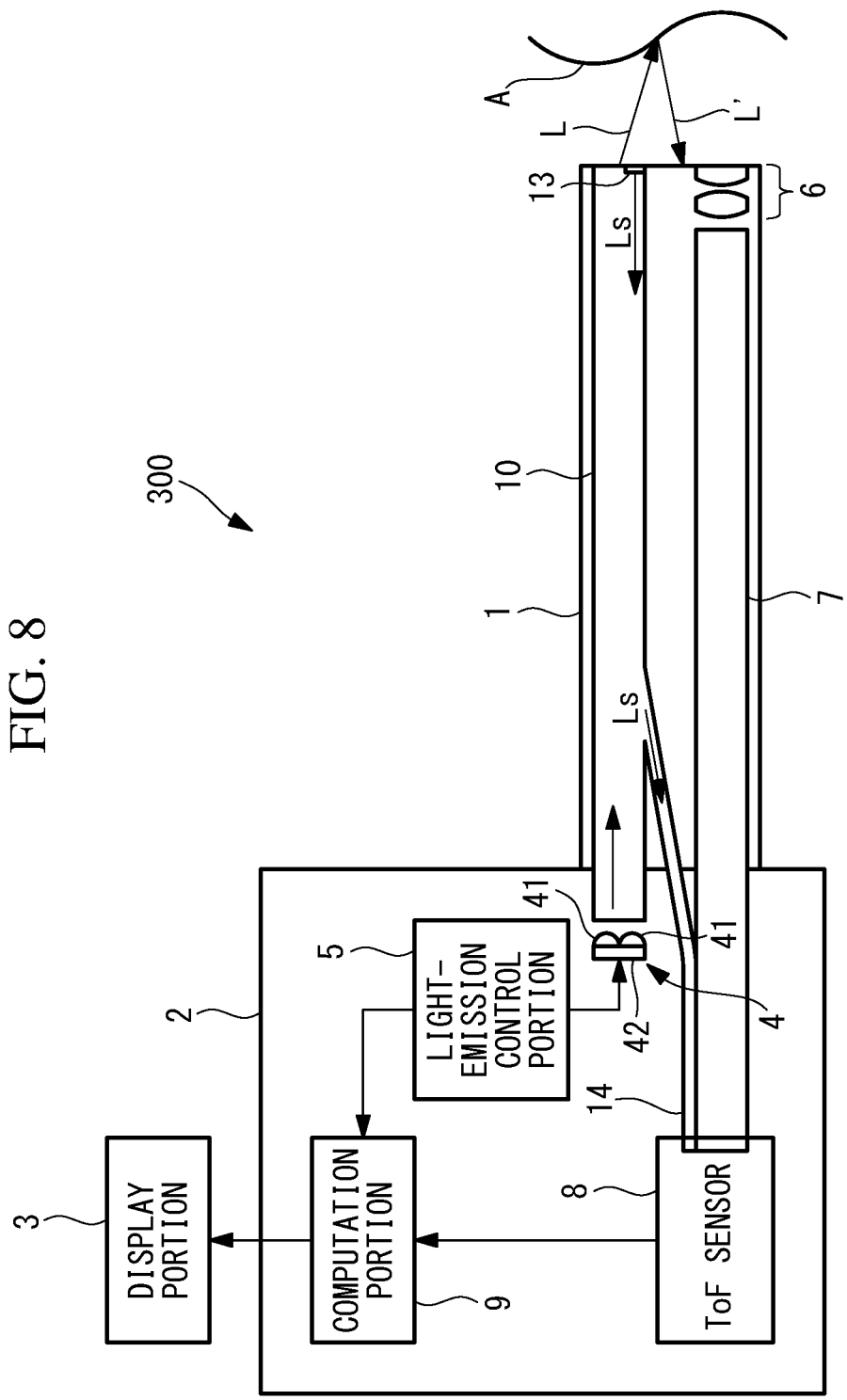
FIG. 8 is an overall configuration diagram of an endoscope apparatus according to a third embodiment of the present invention.

As shown in FIG. 8, an endoscope apparatus 300 according to this embodiment includes: the insertion portion 1; the main body portion 2; and the display portion 3. In addition, the endoscope apparatus 300 includes: the radiating portion 4; the light-emission control portion 5; the imaging optical system 6; the image transmission portion 7; the optical sensor 8; and the computation portion 9.

The radiating portion 4 includes the light guide portion 10, and the light source 41 is disposed inside the main body portion 2. In addition, the radiating portion 4 includes a reference-light generating portion 13 and a reference-light guide portion 14.

The reference-light generating portion 13 is a half mirror that is disposed at the distal end of the light guide portion (first light guide portion) 10. The half mirror is formed, for example, by partially coating a distal-end surface of the light guide portion 10 with a metal. The reference-light generating portion 13 reflects portions of the pulsed light beams L guided by the light guide portion 10. The other portions of the pulsed light beams L guided by the light guide portion 10 are emitted from the distal end of the insertion portion 1. The pulsed light beams L reflected by the reference-light generating portion 13 are guided through the light guide portion 10 toward the proximal end in the form of reference light beams Ls.

The reference-light guide portion (second light guide portion) 14 is, for example, an optical fiber or an optical-fiber bundle and is branched off from an intermediate position in the longitudinal direction of the light guide portion 10. The reference light beams Ls travel into the reference-light guide portion 14 from the light guide portion 10 and are guided to the ToF sensor 8 by the reference-light guide portion 14.

The light receiving surface of the ToF sensor 8 is divided into a first detection region and a second detection region. The reflected light beams L' transmitted by the image transmission portion 7 are made incident in the first detection region and an image of the imaging subject A is formed. The reference light beams Ls guided by the reference-light guide portion 14 are made incident in the second detection region. The respective pixels of the first detection region detect the first light levels S1 and the second light levels S2 of the reflected light beams L', and the respective pixels of the second detection region detect the first light levels (first reference light levels) S1 and the second light levels (second reference light levels) S2 of the reference light beams Ls.

The computation portion 9 calculates the delay times Δt and the observation distances D from the ratios S1/S2 of the light levels S1 and S2 detected by the pixels of the first detection region.

In addition, the computation portion 9 calculates reference delay times Δts from the ratios S1/S2 of the reference light levels S1 and S2 detected by the pixels of the second detection region and calculates reference optical path lengths of the pulsed light beams L and the reference light beams Ls to the ToF sensor 8 from the light source 41 in the insertion portion 1 and the main body portion 2. A reference delay time Δts is a time until a reference light beam Ls reaches the ToF sensor 8 from when the light source 41 generates a pulsed light beam L.

The optical-path lengths of the pulsed light beam L and the reflected light beams L' in the endoscope apparatus 300 could change in accordance with changes in the surrounding environment (for example, temperature and humidity) of the endoscope apparatus 300. Changes in the optical-path lengths of the pulsed light beam L and the reflected light beam L' influence the observation distance D calculated by the computation portion 9, thus causing errors in the observation distance D.

With this embodiment, the optical-path lengths of the reference light beams Ls guided through the endoscope apparatus 300 also change in accordance with the surrounding environment, as with the changes in the optical-path lengths of the pulsed light beams L and the reflected light beams L' in the endoscope apparatus 300. The changes in the optical-path length of the endoscope apparatus 300 are manifested as changes in the reference delay times Δts calculated from the ratios of the first reference light levels S1 to the second reference light levels S2. Therefore, it is possible to correct the errors in the observation distances D caused by the changes in the optical-path lengths of the light beams L and L' in the endoscope apparatus 300 on the basis of the first reference light levels S1 and the second reference light levels S2, more specifically, on the basis of the changes in the reference optical path lengths. For example, the computation portion 9 estimates the amount of change in the optical-path length in the endoscope apparatus 300 by comparing the reference optical path lengths calculated from the reference light levels S1 and S2 with the reference optical path lengths in the standard surrounding environment, and corrects the observation distance D on the basis of the amount of changes in the optical-path length. Accordingly, it is possible to stably measure accurate observation distances D regardless of changes in the surrounding environment.

Fourth Embodiment

Next, am endoscope apparatus according to a fourth embodiment of the present invention will be described with reference to the drawings.

In this embodiment, configurations that are different from those of the first to third embodiments will be described, and configurations that are the same as those of the first to third embodiments will be given the same reference signs and descriptions thereof will be omitted.

Figure 9:
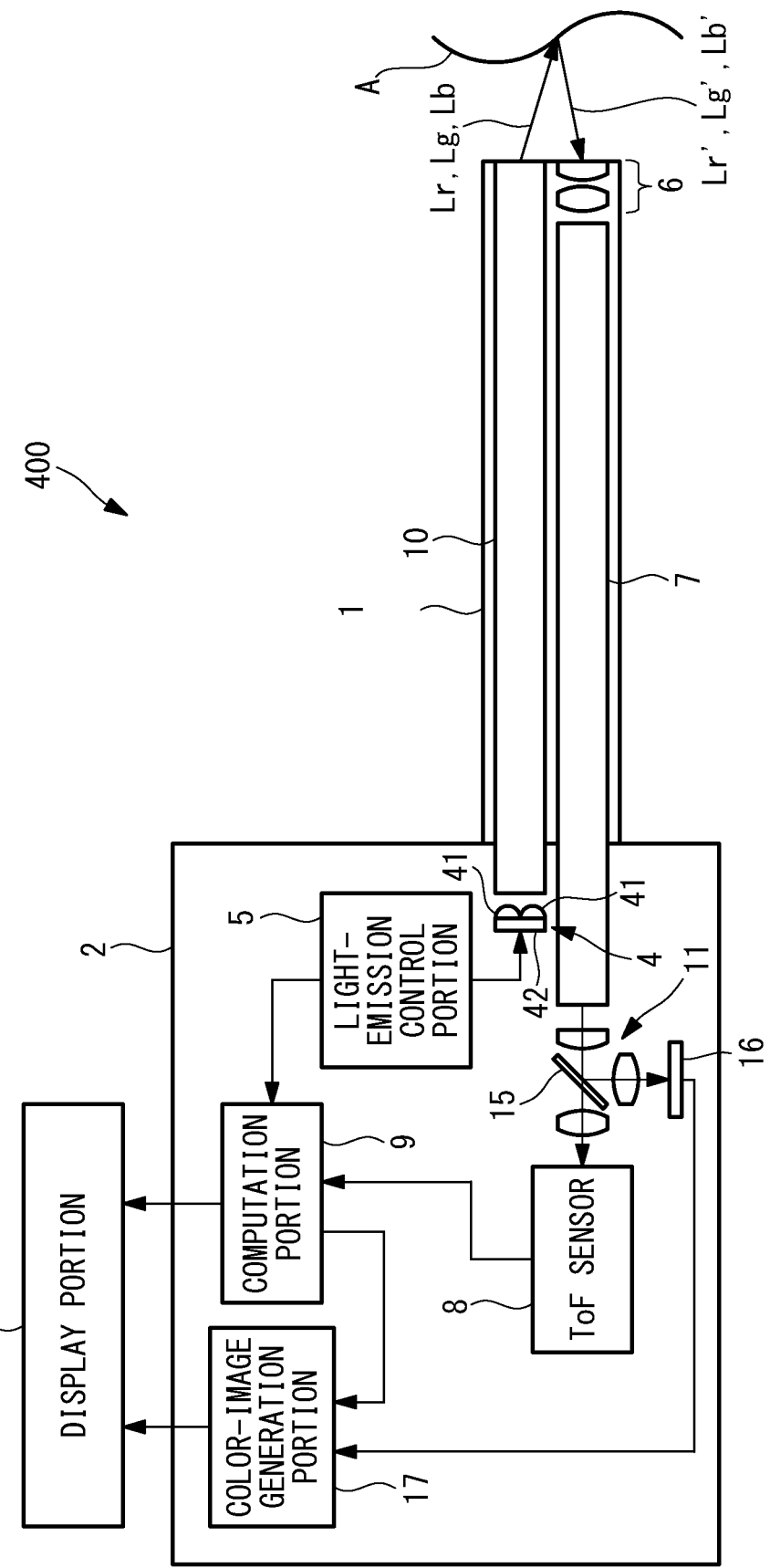
FIG. 9 is an overall configuration diagram of an endoscope apparatus according to a fourth embodiment of the present invention.

As shown in FIG. 9, an endoscope apparatus 400 according to this embodiment includes: the insertion portion 1; the main body portion 2; and the display portion 3. In addition, the endoscope apparatus 400 includes: the radiating portion 4; the light-emission control portion 5; the imaging optical system 6; the image transmission portion 7; the optical sensor 8; the computation portion 9; the re-imaging optical system 11; a color separator 15; an image acquisition device 16; and a color-image generation portion 17.

The radiating portion 4 includes the light guide portion 10, and the light source 41 is disposed inside the main body portion 2. The light source 41 generates red (R), green (G), and blue (B) light beams Lr, Lg, and Lb. The R light beam Lr is a pulsed light beam for measuring the observation distance D. The G light beam Lg and the B light beam Lb are continuous light beams for acquiring an image of the imaging subject A. In the imaging subject A, pulsed R reflected light beam Lr', as well as G reflected light beam Lg' and B reflected light beam Lg', which are continuous light beams, are generated.

The color separator 15 is disposed between the image transmission portion 7 and the ToF sensor 8. The color separator 15 separates the R reflected light beam Lr' and the G and B reflected light beams Lg' and Lb' from each other according to the wavelengths thereof. The color separator 15 is, for example, a dichroic mirror that allows red light beams to pass therethrough and that reflects green and blue light beams. The R reflected light beam Lr' is made incident on the ToF sensor 8 from the color separator 15, the G reflected light beam Lg' and the B reflected light beam Lb' are made incident on the image acquisition device 16 from the color separator 15.

The re-imaging optical system 11 causes the R reflected light beam Lr' to be re-imaged on the light receiving surface of the ToF sensor 8 and causes the G reflected light beam Lg' and the B reflected light beam Lb' to be re-imaged on the light receiving surface of the image acquisition device 16.

The image acquisition device 16 is an RGB-type two-dimensional image sensor such as a CMOS image sensor. The image acquisition device 16 acquires images of the imaging subject A and generates image signals. The image signals are transmitted to the color-image generation portion 17 from the image acquisition device 16.

The color-image generation portion 17 generates a two-dimensional color image of the imaging subject A from the image signals. The color image is displayed on the display portion 3 together with the distance map. The color image and the distance map may be transmitted to the display portion 3 after being associated with each other in the main body portion 2.

The color-image generation portion 17 is realized by means of the processor and the storage device provided inside the main body portion 2, as with the light-emission control portion 5 and the computation portion 9. In other words, the processor executes the image generation processing by the color-image generation portion 17 in accordance with the image generation program stored in the storage device.

As has been described above, with this embodiment, the continuous light beams Lg and Lb having different colors from the pulsed light beam Lr are radiated onto the imaging subject A simultaneously with the pulsed light beam Lr, and, as a result of separating the reflected light beam Lr' and the reflected light beams Lg' and Lr' from each other in accordance of the colors thereof, there is an advantage in that it is possible to acquire a color image of the imaging subject A simultaneously with the measurement of the observation distance D.

In this embodiment, the R light beam Lr is employed in measuring the observation distance D; however, the wavelength of the pulsed light beam for measuring the observation distance D is not limited thereto, and a pulsed light beam of an arbitrary wavelength that is different from the wavelengths of the continuous light beams for acquiring images may be employed.

Figure 10:
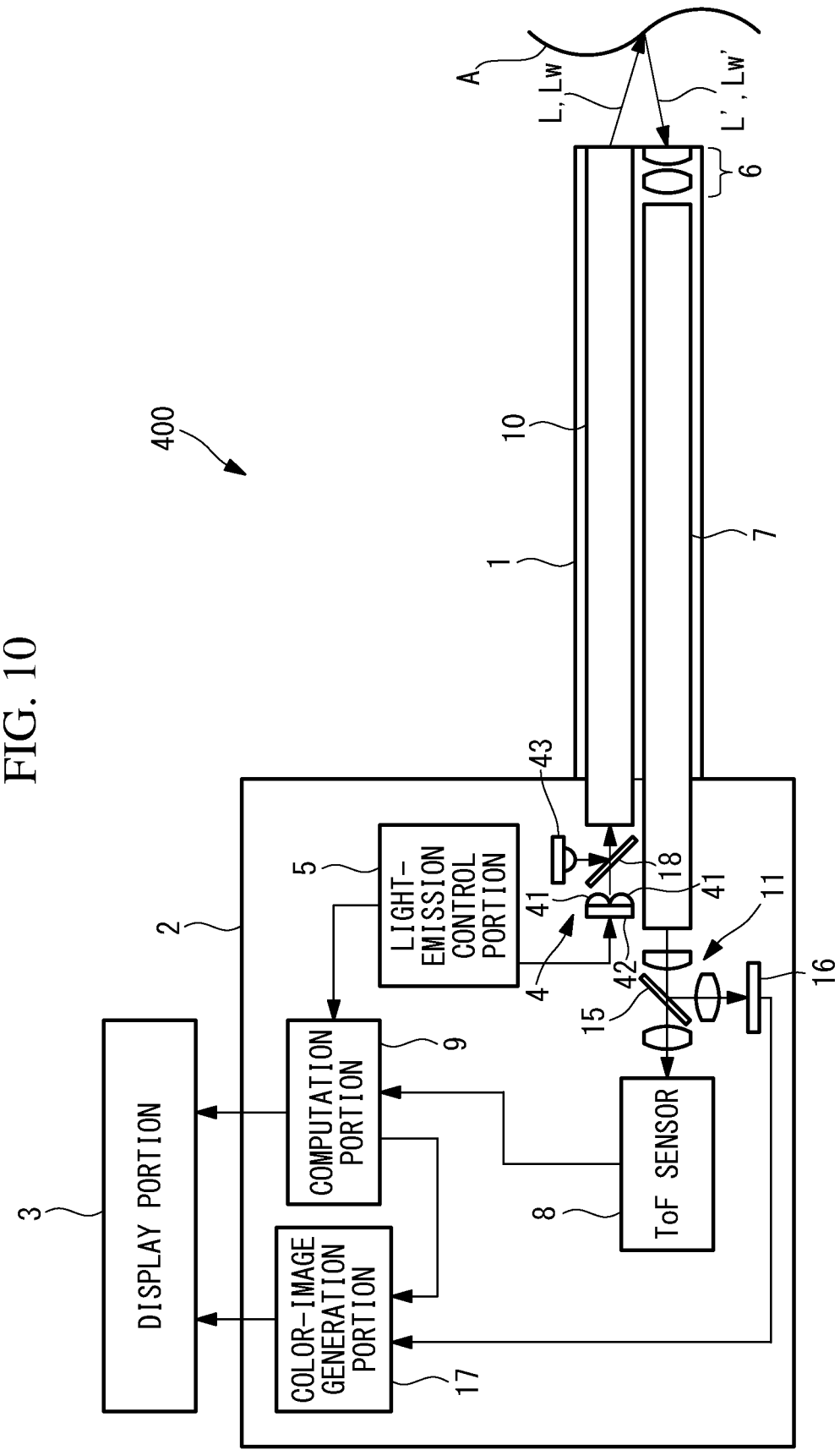
FIG. 10 is an overall configuration diagram of a modification of the endoscope apparatus in FIG. 9.

In this embodiment, the radiating portion 4 may additionally include a white light source 43 that generates a white light beam Lw, as shown in FIG. 10. The white light beam Lw is a continuous light beam. The pulsed light beam L is a light of wavelength other than those in the visible range and is, for example, infrared light. A color combining element 18 is disposed between the two light sources 41 and 43 and the light guide portion 10. The color combining element 18 combines the pulsed light beam L coming from the light source 41 and the white light beam Lw coming from the white light source 43. The color combining element 18 is, for example, a dichroic mirror.

The color separator 15 separates the reflected light beam L' of the pulsed light beam L and the reflected light beam Lw' of the white light beam Lw from each other according to the wavelengths thereof. The reflected light beam L' is made incident on the ToF sensor 8 from the color separator 15 and the reflected light beam Lw' is made incident on the image acquisition device 16 from the color separator 15.

With the modification in FIG. 10, as a result of employing the white light beam Lw, it is possible to acquire a white light image that contains a larger quantity of color information of the imaging subject A by means of the image acquisition device 16.

Figure 11:
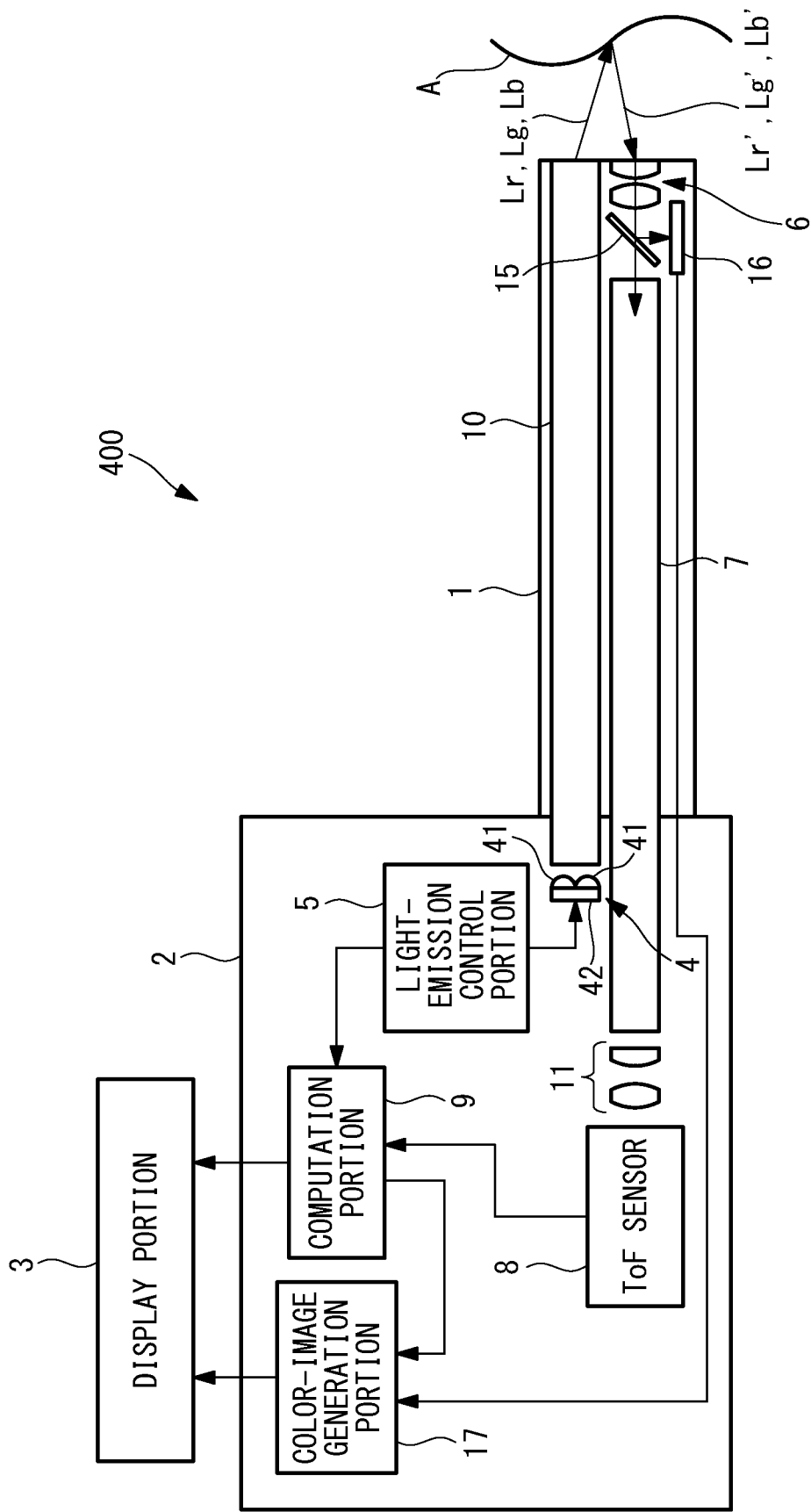
FIG. 11 is an overall configuration diagram of another modification of the endoscope apparatus in FIG. 9.
Figure 12:
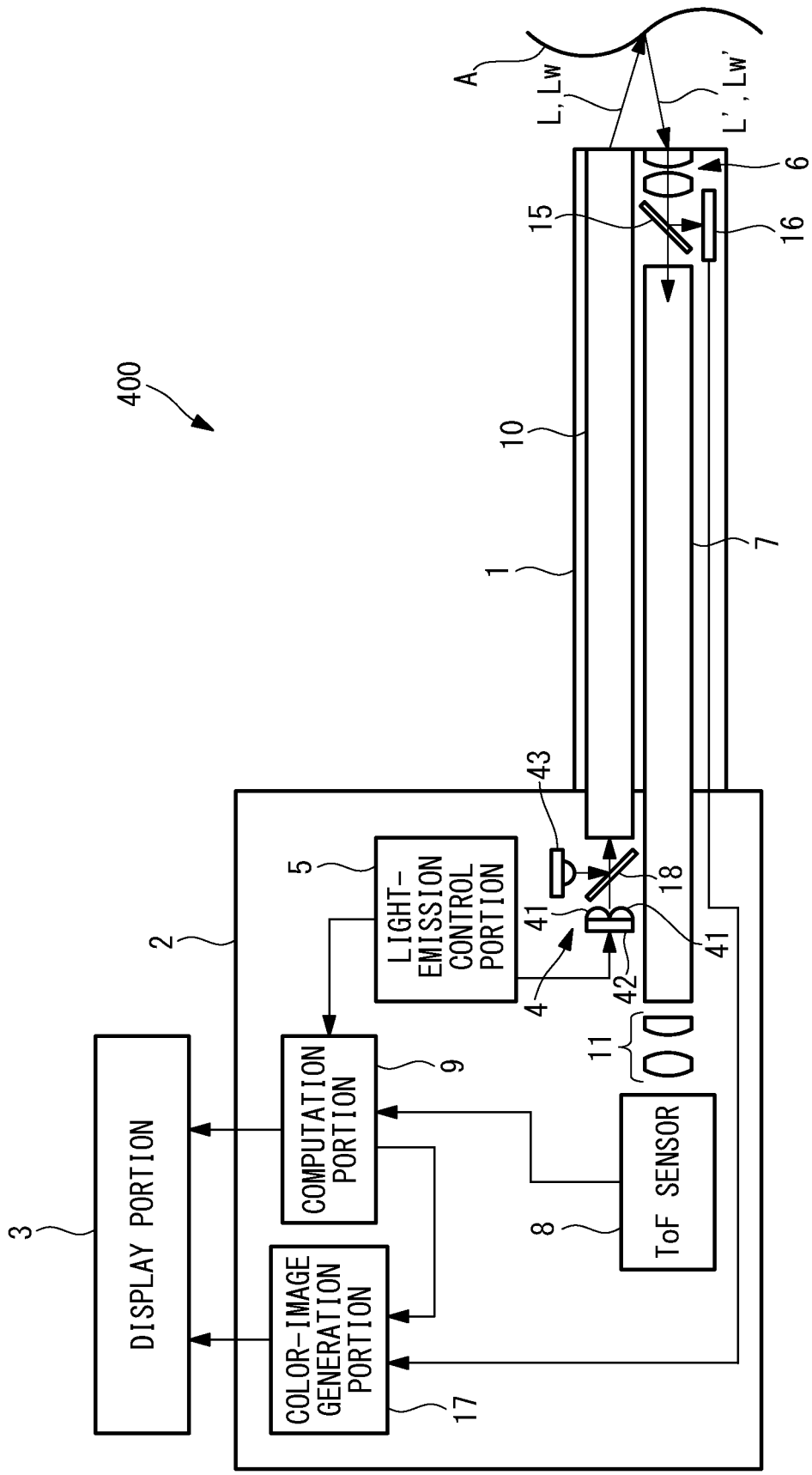
FIG. 12 is an overall configuration diagram of another modification of the endoscope apparatus in FIG. 9.

As shown in FIGS. 11 and 12, this embodiment may be configured so that the color separator 15 and the image acquisition device 16 are disposed between the imaging optical system 6 and the image transmission portion 7 in the distal-end portion of the insertion portion 1 and so that only the reflected light beam L' of the pulsed light beam L is made incident on the image transmission portion 7 from the color separator 15.

Figure 13:
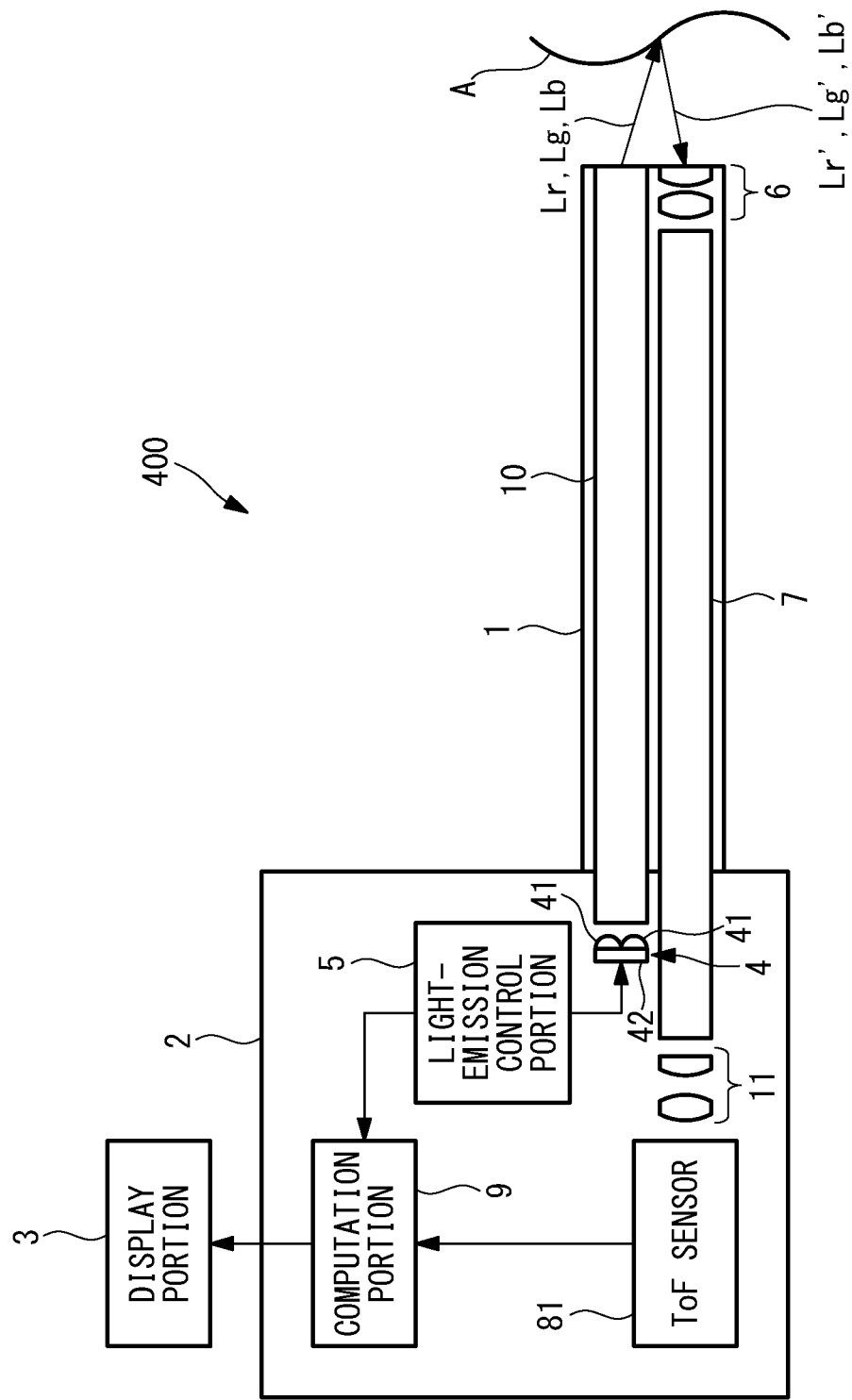
FIG. 13 is an overall configuration diagram of another modification of the endoscope apparatus in FIG. 9.

As shown in FIG. 13, in this embodiment, a ToF sensor 81 having a color separation function may be employed instead of the color separator 15 and the image acquisition device 16.

Figure 14:
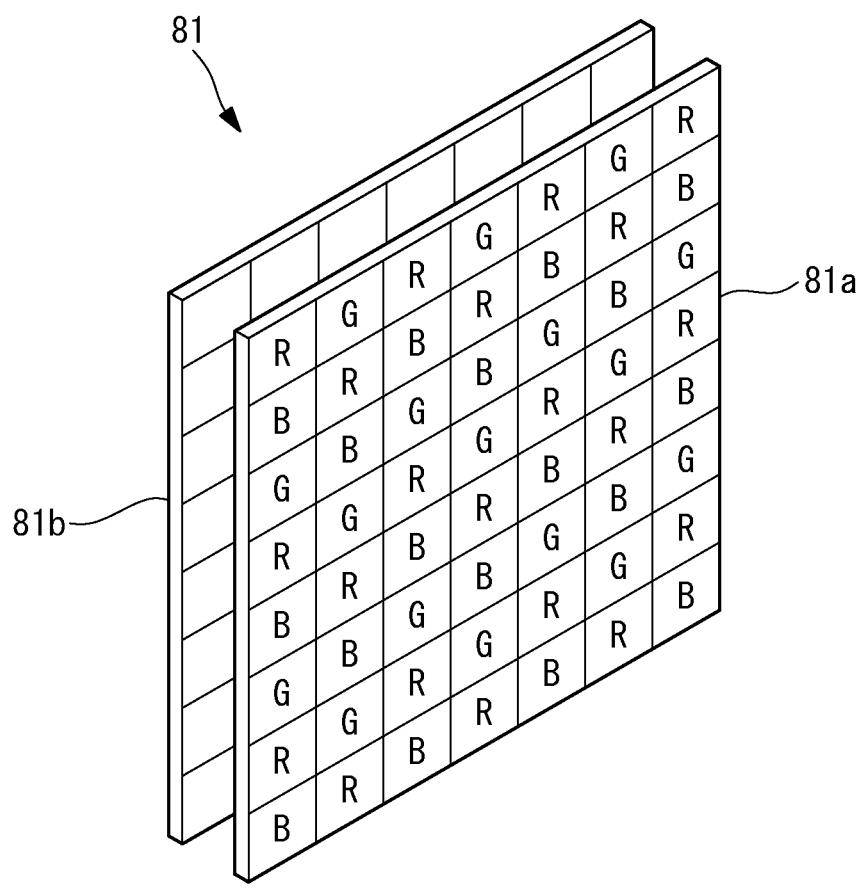
FIG. 14 is a diagram showing an example of a ToF sensor equipped with a color filter array in the endoscope apparatus in FIG. 13.

As shown in FIG. 14, the ToF sensor 81 having a color separation function includes a color filter array 81a that covers a two-dimensional array 81b of pixels.

The color filter array 81a is a two-dimensional array of R filters, G filters and B filters. The R filters, the G filters, and the B filters respectively allow red, green, and blue light beams to pass therethrough in a selective manner. In other words, the ToF sensor 81 also serves as an RGB-type two-dimensional image sensor. The reflected light beams Lr', Lg', and Lb' of all colors are made incident on the ToF sensor 81.

In the modification in FIG. 13, at least one of the R light beams Lr, the G light beams Lg, and the B light beams Lb are pulsed light beams. For example, in the case in which the R light beams Lr are pulsed light beams, the computation portion 9 calculates the observation distances D from the ratios S1/S2 of the R pixels. In addition, the computation portion 9 calculates the sums S1+S2 of the respective pixels so as to serve as signal values, generates an RGB color image on the basis of the signal values, and causes the display portion 3 to display the color image.

All of the R light beams Lr, the G light beams Lg, and the B light beams Lb may be pulsed light beams, and the computation portion 9 may calculate the observation distances D from the ratios S1/S2 of all of the R, G, and B pixels.

The light levels of the R reflected light beams Lr', the G reflected light beams Lg', and the B reflected light beams Lb' could differ from each other. One of the R reflected light beam Lr', the G reflected light beam Lg', and the B reflected light beam Lb' with which it is possible to obtain optimal light levels S1 and S2 is selected, and the observation distance D is calculated from the ratio S1/S2 of the selected reflected light beam. Accordingly, it is possible to measure the observation distance D at a higher precision.

In addition, in the case of an imaging subject A possessing light transmitting properties, such as biological tissue, due to the fact that the transmission depths of the pulsed light beams Lr, Lg, and Lb in the imaging subject A are different from each other, the observation distances D are also different among R, G, and B. As a result of comparing the observation distances D among R, G, and B, it is possible to assess the optical characteristics of the imaging subject A. Accordingly, it is possible to identify, for example, a region in which the optical characteristics are different from those of surrounding areas, such as cancer tissue. The identified region may be displayed on the distance map or the color image on the display portion 3.

As a result, the above-identified embodiments lead to the following aspect.

An aspect of the present invention is an endoscope apparatus including: a radiating portion that radiates a pulsed light beam onto an imaging subject from a distal end of an insertion portion; an imaging optical system that is disposed at a distal-end portion of the insertion portion and that forms an image of the imaging subject by imaging a reflected light beam of the pulsed light beam coming from the imaging subject; an image transmission portion that is disposed along a longitudinal direction inside the insertion portion and that transmits the image of the imaging subject to a proximal-end side of the insertion portion; an optical sensor that has a light receiving surface on which a plurality of pixels are arrayed and that detects, by means of each of the plurality of pixels, a light level of the image transmitted to the light receiving surface by the image transmission portion; and a computation portion that calculates an observation distance to the imaging subject from the imaging optical system on the basis of the light level detected by each of the plurality of pixels, wherein the optical sensor obtains a first light level and a second light level by detecting, in a time division manner, the reflected light beam at each of the pixels, the first light level is the light level of the reflected light beam accumulated during a first period, and the second light level is the light level of the reflected light beam accumulated during a second period, and wherein the computation portion calculates the observation distance to each of the positions of the imaging subject from the imaging optical system on the basis of the first light level and the second light level, which are detected by the optical sensor at each of the pixels.

The present invention affords an advantage in that it is possible to measure distances to a plurality of positions of an imaging subject without scanning laser light and it is possible to measure short observation distances at a high precision.

REFERENCE SIGNS LIST

1 insertion portion
2 main body portion
3 display portion
4 radiating portion
41 light source (radiating portion)
42 control circuit (radiating portion)
43 white light source (radiating portion)
5 light-emission control portion
6 imaging optical system
7 image transmission portion
8 optical sensor, ToF sensor
9 computation portion
10 light guide portion (radiating portion, first light guide portion)
11 re-imaging optical system
12 adjustment portion
13 reference-light generating portion
14 reference-light guide portion (radiating portion, second light guide portion)
15 color separator
16 image acquisition device
17 color-image generation portion
18 color combining element
100,200,300,400 endoscope apparatus
A imaging subject

The invention claimed is:

1. An endoscope apparatus comprising:
an insertion portion;
a light source configured to radiate a pulsed light beam onto an imaging subject;
an imaging optical system disposed at a distal end of the insertion portion and configured to form an image of the imaging subject based on a reflected light beam of the pulsed light beam coming from the imaging subject;
an image transmission optical system disposed along a longitudinal direction of the insertion portion and configured to transmit the image of the imaging subject;
an optical sensor comprising a plurality of pixels arrayed on a light receiving surface, the optical sensor being configured to detect a first light level of a first reflected light beam accumulated during a first period and a second light level of a second reflected light beam accumulated during a second period; and
one or more processors comprising hardware configured to:
calculate a distance based on the first light level and the second light level; and
subtract a correction value from the calculated distance, the correction value being set on a basis of the depth to which the pulsed light beam is transmitted into the imaging subject.

2. The endoscope apparatus according to claim 1, wherein a pulse width of the pulsed light beam is greater than a value obtained by dividing a product of a refractive index of the image transmission optical system and a length of the image transmission optical system by a light speed of the pulsed light beam.

3. The endoscope apparatus according to claim 1, wherein the one or more processors are configured to adjust, on a basis of the first light level and the second light level, at least one of lengths of the first period and the second period, and a pulse width of the pulsed light beam,
wherein, in response to a ratio of the first light level to the second light level being equal to or greater than a prescribed upper limit value, the one or more processors are configured to increase the lengths of the first and second periods and/or decrease the pulsed width of the pulsed light beam, and
wherein, in response to the ratio of the first light level to the second light level being equal to or less than a prescribed lower limit value, the one or more processors are configured to decrease the lengths of the first and second periods and/or increase the pulse width of the pulsed light beam.

4. The endoscope apparatus according to claim 3, wherein in response to a ratio of the first light level to the second light level being between the prescribed upper limit value and the prescribed lower limit value, the one or more processors are configured to calculate the distance.

5. The endoscope apparatus according to claim 1, wherein the one or more processors are configured to adjust, on a basis of the first light level and the second light level, a light level of the pulsed light beam, and
wherein the one or more processors are configured to decrease the light level of the pulsed light beam in response to a sum of the first light level and the second light level being equal to or greater than a prescribed upper limit value and increase the light level of the pulsed light beam in response to the sum of the first light level and the second light level being equal to or less than a prescribed lower limit value.

6. The endoscope apparatus according to claim 1, wherein the light receiving surface of the optical sensor has a first detection region in which a light level of the image of the imaging subject is detected and a second detection region that is different from the first detection region and in which a light level of a reference light beam is detected, wherein each pixel of the second detection region detects a first reference light level by accumulating the light level of the reference light beam during the first period and detects a second reference light level by accumulating the light level of the reference light beam during the second period, and wherein the one or more processors are further configured to correct the observation distance on a basis of the first reference light level and the second reference light level.

7. The endoscope apparatus according to claim 1, further comprising a re-imaging optical system that is disposed between the image transmission optical system and the optical sensor and that transmits the image transmitted thereto by the image transmission portion to the optical sensor.

8. The endoscope apparatus according to claim 1, wherein the light source is disposed at the distal end of the insertion portion.

9. A method for operating an endoscope apparatus comprising:
an insertion portion;
a light source configured to radiate a pulsed light beam onto an imaging subject;
an imaging optical system disposed at a distal end of the insertion portion and configured to form an image of the imaging subject based on a reflected light beam of the pulsed light beam coming from the imaging subject;
an image transmission optical system disposed along a longitudinal direction of the insertion portion and configured to transmit the image of the imaging subject; and
an optical sensor comprising a plurality of pixels arrayed on a light receiving surface, the optical sensor being configured to detect a first light level of a first reflected light beam accumulated during a first period and a second light level of a second reflected light beam accumulated during a second period,
wherein the method comprises:
calculating a distance based on the first light level and the second light level; and
subtracting a correction value from the calculated distance, the correction value being set on a basis of the depth to which the pulsed light beam is transmitted into the imaging subject.

10. The method for operating the endoscope apparatus according to claim 9,
wherein a pulse width of the pulsed light beam is greater than a value obtained by dividing a product of a refractive index of the image transmission optical system portion and a length of the image transmission optical system by a light speed of the pulsed light beam.

11. The method for operating the endoscope apparatus according to claim 9, wherein the one or more processors are further configured to adjust, on a basis of the first light level and the second light level, at least one of lengths of the first period and the second period, and a pulse width of the pulsed light beam, wherein, in response to a ratio of the first light level to the second light level being equal to or greater than a prescribed upper limit value, the one or more processors are configured to adjusting of the at least one of the lengths and the pulse width increases increase the lengths of the first and second periods and/or decrease decreases the pulsed width of the pulsed light beam, and wherein, in response to the ratio of the first light level to the second light level being equal to or less than a prescribed lower limit value, the one or more processors are configured to the adjusting of the at least one of the lengths and the pulse width decreases decrease the lengths of the first and second periods and/or increase increases the pulse width of the pulsed light beam.

12. The method for operating the endoscope apparatus according to claim 9,
wherein the one or more processors are further configured to adjust, on a basis of the first light level and the second light level, a light level of the pulsed light beam, and
wherein the one or more processors are configured to decrease the adjusting of the light level decreases the light level of the pulsed light beam in response to a sum of the first light level and the second light level being equal to or greater than a prescribed upper limit value and increase increases the light level of the pulsed light beam in response to the sum of the first light level and the second light level being equal to or less than a prescribed lower limit value.

13. An endoscope main body comprising:
an optical sensor comprising a plurality of pixels arrayed on a light receiving surface, the optical sensor being configured to detect a first light level of a first reflected light beam accumulated during a first period and a second light level of a second reflected light beam accumulated during a second period,
one or more processors comprising hardware configured to:
calculate a distance based on the first light level and the second light level; and
subtract a correction value from the calculated distance, the correction value being set on a basis of the depth to which a pulsed light beam is transmitted into an imaging subject.

* * * * *